United States Patent [19]

Giard et al.

[11] 4,357,422

[45] Nov. 2, 1982

[54] METHOD OF ENHANCING INTERFERON PRODUCTION

[75] Inventors: Donald J. Giard, Bedford; Robert J. Fleischaker, Jr., Cambridge, both of Mass.

[73] Assignee: Massachusetts Institute of Technology, Cambridge, Mass.

[21] Appl. No.: 177,945

[22] Filed: Aug. 14, 1980

[51] Int. Cl.$^3$ .............................................. C12P 21/00
[52] U.S. Cl. ..................................... 435/68; 435/811; 435/240; 435/948; 435/183; 424/85
[58] Field of Search ..................... 435/68, 70, 71, 229, 435/41, 183, 240, 195, 230, 92, 43, 234, 211

[56] References Cited

U.S. PATENT DOCUMENTS

| 3,892,629 | 7/1975 | Smith et al. | 435/234 |
| 4,189,534 | 2/1980 | Levine et al. | 435/2 |
| 4,198,479 | 4/1980 | Tytell et al. | 435/68 |

OTHER PUBLICATIONS

Atherton et al., J. Gen. Virol. 41, 229–237, 1978.
The Boston Globe, Mar. 20, 1980, pp. 1 and 9.
Havell et al., N.I.H. Report No. IDB-ASP-02-058, Feb. 18, 1973.
Myers et al., J. Nat. Cancer Inst. 47, No. 4, 757–763, 1971.
Paucker et al., N.I.H. Grant No. NIH 70-2172, Annual Reports, Jun. 1971 and Jun. 1972.
Sypula et al., Archiuum Immunologiae et Therapiae Experimentalis 26, 499–501, 1978.
Stinebring et al., Human Interferon, 1978, pp. 15–21, 40 and 56–57.
Prescott et al., Industrial Microbiology, 1959, pp. 499–500, 611, 620–621.
Peppler, Microbial Technology, 1967, pp. 300, 373.
Kojima et al., Japan. J. Microbiol., vol. 183, pp. 217–222, 1974.
Maehara et al., Microbiol. Immunol., vol. 24, (10) pp. 907–914, 1980.

*Primary Examiner*—Alvin E. Tanenholtz
*Assistant Examiner*—John Edward Tarcza
*Attorney, Agent, or Firm*—Arthur A. Smith, Jr.; David E. Brook

[57] ABSTRACT

A method for enhancing the production of interferon from normal human diploid fibroblast cells is disclosed. In this method, a distinct interferon-production phase is established in which the temperature is initially elevated for a brief period followed by a reduction in temperature for the balance of the interferon-production phase.

15 Claims, 5 Drawing Figures

METHOD OF ENHANCING INTERFERON PRODUCTION

SUPPORT

Work described herein was supported by grants or contracts from the National Science Foundation, the National Institutes of Health, and the Lewis and Rosa Strauss Memorial Foundation.

DESCRIPTION

1. Technical Field

This invention is in the field of cell biology.

2. Background Art

Interferon can be defined as an induced protein, probably a glycoprotein, that produces a characteristic antiviral state upon incubation with component cells. Interferon is released by animal cells following viral infection and also after treatment of such cells with certain non-viral inducers. It constitutes one of the major defense mechanisms against viral infections in mammals, including humans. In addition, interferon has been found to have immunoregulatory activities, to affect various cellular functions, including cell division, and to have potential value as an anticancer drug.

It is known that there are at least three distinct species of human interferon. Each of these has been named from their major source. Thus, Le interferon is the major interferon species produced in cells of lymphoid origin, such as leukocytes; F interferon is the predominant interferon species obtained from non-lymphoid cells, such as fibroblasts; and T-type or immune interferon is preferentially produced in cultures of lymphocytes, particularly such cultures enriched for T cells.

To date, it has been difficult to obtain adequate amounts of any species of interferon to properly evaluate its clinical potential. The species of interferon most widely used in clinical trials to date is the Le interferon produced by the leukocyte/New Castle Disease virus (NDV) system. See Strander, H. and Cantell, K. in "The Production and Use of Interferon for the Treatment and Prevention of Human Virus Infections," C. Weymouth, Ed., Tissue Culture Association, Rockville, Md., USA, pp. 4-11, 1974. The leukocyte/NDV system has certain drawbacks, however, which include the limited supply of leukocytes and the risk of viral contamination, such as with Hepatitis virus. Because of this, much research effort has been directed to producing other species of interferon, particularly F interferon.

Production of F interferon employing human fibroblasts has certain advantages. Because the cells can be grown in cell cultures, for example, scale-up is possible. Additionally, cell stocks can be continuously monitored to insure the absence of pathogens and a normal karyotype. Also, fibroblasts can be induced to produce interferon employing non-viral inducers.

Such research has involved the testing of many different types of fibroblast cells and cell lines. Additionally, much effort has been directed towards varying the experimental culture conditions including the number of cells employed, the ingredients in the culture medium, the temperature employed for incubation and production, and other such parameters of the growth processes. Techniques such as priming interferon-producing cells with small amounts of interferon and superinduction employing antimetabolites have evolved from such research. While priming, superinduction, and other recently discovered techniques have improved interferon production considerably, much greater increases in productivity are still required.

DISCLOSURE OF THE INVENTION

This invention relates to a method of enhancing interferon production, particularly interferon production by fibroblast cells. In its most general sense, this invention relates to the establishment of a distinct interferon-production phase in which the temperature is initially elevated for a short period of time and then subsequently reduced to a selected interferon-production temperature capable of sustaining interferon production for prolonged periods. The invention can be practiced by forming a cell culture of interferon-producing cells and introducing an interferon-inducer into the culture in an amount sufficient to induce interferon production. In a particularly preferred embodiment, the fibroblast cells are cultured on microcarriers suspended in cell culture medium. One method by which the distinct production phase can be established is by introducing one or more antimetabolites to effectively block interferon production during the induction period and subsequently removing the antimetabolites to initiate the distinct interferon-production phase.

This interferon-production phase is initiated at a first temperature, such as 37° C., but after a short period, the temperature is reduced to a lower temperature, such as 30° C. The initial elevation in temperature, in combination with the subsequent reduced temperature, allows interferon production to be sustained at high rates and for prolonged periods compared to the rates and periods if a uniform temperature is employed during production. Often, the rate of interferon production is increased during the period of elevated temperature. More surprising, however, is the fact that the rate of interferon production is elevated compared to the rate which would exist if production was carried out at a uniform temperature. Additionally, interferon production is usually prolonged when the temperature shift is employed. As a result, interferon productivity is improved and total interferon yield is increased significantly by a simple temperature shift during the distinct production phase.

BEST MODE FOR CARRYING OUT THE INVENTION

For the work described herein, interferon activity was assayed by determining the 50% level of cell protection for samples and standard solutions using FS-4 cells challenged with Vesicular Stomatitis Virus (VSV), Indiana strain. See, Havell, E. A. and Vilcek, J., "Production of High-Titered Interferon in Cultures of Human Diploid Cells," *Antimicrobial Agents and Chemotherapy*, 2, pp. 476-84, 1972. Interferon titers are determined by including internal standards calibrated against International Standard GO23-901-527 (obtained from The National Institutes of Health, Bethesda, Md.) in each assay.

The cells employed in the experimental work described herein were human diploid foreskin cells designated as FS-4 cells. These are known to be good producers of F-interferon and probably also produce some L interferon. Other normal human diploid cell strains, which might be employed, include embryonic lung fibroblasts, such as WI-38, MRC-5, RS-48, and IMR-90, foreskin fibroblasts, such as FS-49; and even human non-fibroblast cell strains, including epithelial and kidney cells. In addition, it is believed that certain established cell lines would be suitable, including such lines as HT-1376 (bladder carcinoma); MG-63 (osteosarcoma-derived); 108 (SV40 transformed WI-38); etc. Generally, it is believed that any mammalian cell strain or line which produces interferon can be employed.

The preferred culturing techniques involve the use of microcarrier cultures. Microcarrier cultures offer many potential advantages including ease of innovative cellular manipulation and potential high density cell growth in very limited volumes. A specific example of microcarriers found suitable are those cell culture microcarriers sold under the trademark "Superbead" by Flow Laboratories, McLean, Virginia. An extensive description of such microcarriers and their use in cell cultures is presented in U.S. Pat. No. 4,189,534, issued to David W. Levine et al., the teachings of which are hereby incorporated by reference.

Such microcarrier cultures employ standard cell culture media, such as Dulbecco's Modified Eagle Medium (DMEM), RPMI-1640 medium, Weymouth's 199, etc. Serum supplement is usually added, but it was found that the growth of FS-4 cells in microcarrier culture required less serum than generally employed with other culturing systems, such as roller bottles.

Figure 1:
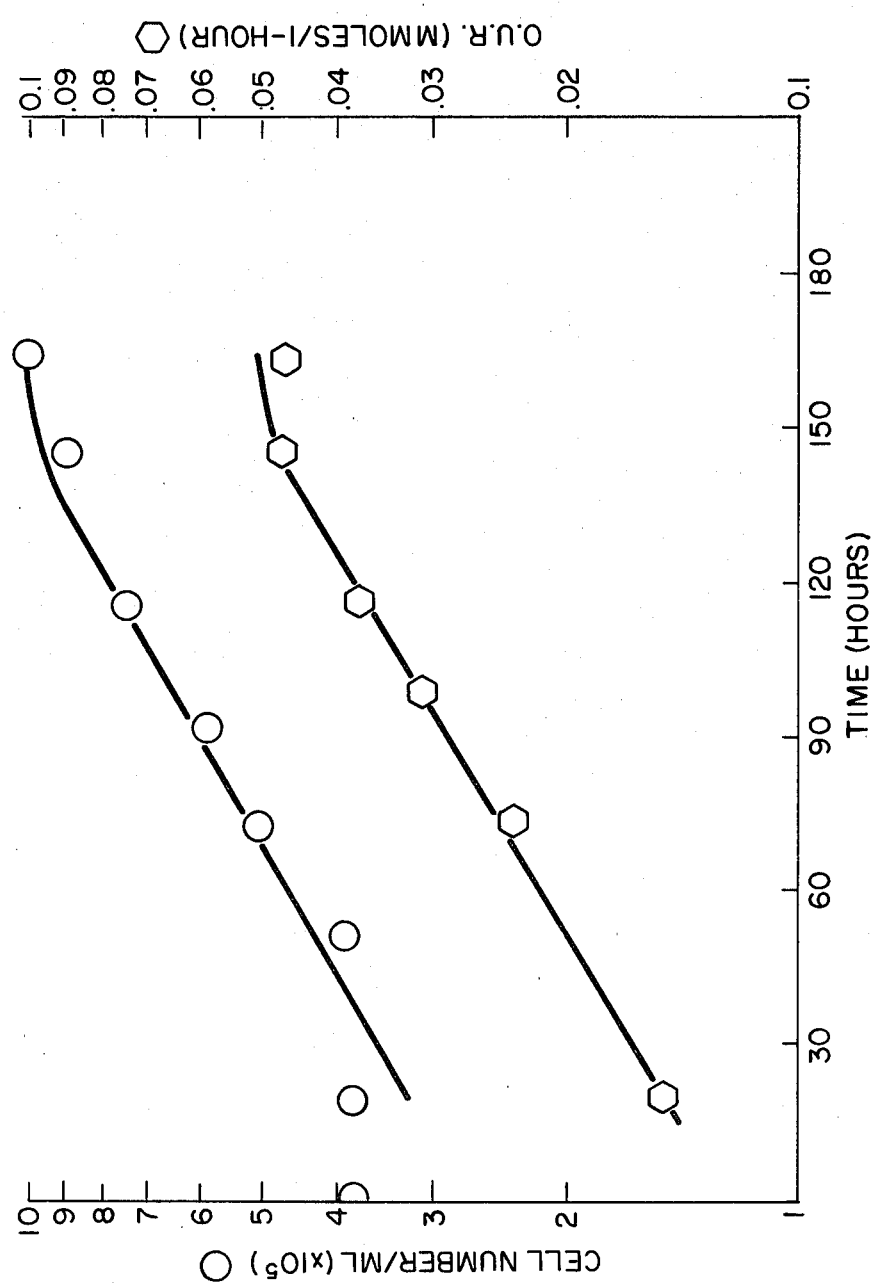
FIG. 1 is a plot graphically illustrating the growth characteristics of a 5-liter FS-4 fibroblast cell culture at a microcarrier concentration of 5 grams per liter.

It was found that good growth of FS-4 cells could be routinely achieved if careful attention was paid to the preparation of the inoculum and to control of the cell density at inoculation, despite previous findings that normal human cells were sometimes more difficult to grow on microcarriers than most cell lines. One example of a technique which was found to be consistently successful employed an inoculum grown in Corning 490 plastic roller bottles using DMEM supplemented with 10% fetal bovine serum (FBS). Confluent FS-4 cells in roller bottles, not older than 4 weeks, were split 1:2 and grown in roller bottles and then harvested. These cells were then used to inoculate microcarrier cultures. In order to obtain uniform growth of cells on the microcarriers, it was found that the cells should be well dispersed and that it was desirable to exceed a certain minimum requirement of cells per surface area. As an example, it was found preferable, at a microcarrier concentration of 5 grams/liter, to have an inoculum density of $3 \times 10^5$ cells/ml or more. Also, as previously mentioned, the FBS concentration was reduced from 10% to 5% in order to promote good attachment of cells to the microcarriers during the stationary growth phase and during the interferon induction and production phases. FIG. 1 illustrates a typical growth curve of the FS-4 cells under such conditions, as more completely described in Example 1, below.

Although microcarrier cultures were employed in work described herein, and are preferred, any other existing cell culturing technique can be employed. Thus, petri dishes, prescription bottles, roller tubes, roller bottles, etc., can be employed for anchorage-dependent cells and suspension cultures can be employed for those cells capable of growing in direct suspensions.

Priming, which is the addition of a small amount of interferon prior to induction, was found to be useful with the FS-4 cells grown in microcarrier cultures. In general, low amounts of interferon, such as 50 units/ml medium, are employed. In addition to enhancing production, priming appeared to add consistency to the results achieved. Priming is normally carried out by adding the small amount of interferon prior to adding an interferon inducer to the cell culture. Priming has been described in the literature, and has been found to help in some cases, but not all. See, for example, Havell, E. A. and Vilcek, J., cited above; and Myers, M. W. and Friedman, R. M., "Potential of Human Interferon Production by Superinduction," *J. Nat. Cancer Inst.*, 47, No. 4, 757–63, (1971).

Induction of the FS-4 cells was achieved using the known interferon inducer, polyinosinic-polycytidylic acid (poly I-poly C). Other synthetic inducers, such as Poly I, Poly I-Poly C-Polylysine and Poly I-Poly C-DEAE Dextran could also be employed. Additionally, viral inducers including Sendai Virus, New Castle Disease Virus (NDV) and others, could be employed, live or inactivated (such as by irradiation with UV light). These inducers are all known to those skilled in the art. See, for example, Havell and Vilcek, cited above.

Superinduction techniques were employed in the work described. Generally, superinduction involves the addition of antimetabolites to an induced cell culture to prevent interferon production until the antimetabolite is removed. This also separates the process into distinct interferon-induction and interferon-production phases.

Specifically, a superinduction technique employing both cycloheximide and actinomycin-D was employed. Whereas previous work had used 50 $\mu$g/ml of cycloheximide, studies undertaken in conjunction with this work indicated that lower amounts produced better yields. As a result, the concentration for cycloheximide was lowered and 10 $\mu$g/ml is the specific concentration which was used in much of the work.

Similarly, the effect of actinomycin-D concentration was studied from 0 to 2 $\mu$g/ml, and there were no significant differences found for concentrations ranging between from about 0.25 and 2.0 $\mu$g/ml. However, lowering the concentration below 0.125 $\mu$g/ml resulted in a two-fold drop in interferon yield. Thus, the concentration of 1 $\mu$g/ml was chosen.

Figure 2:
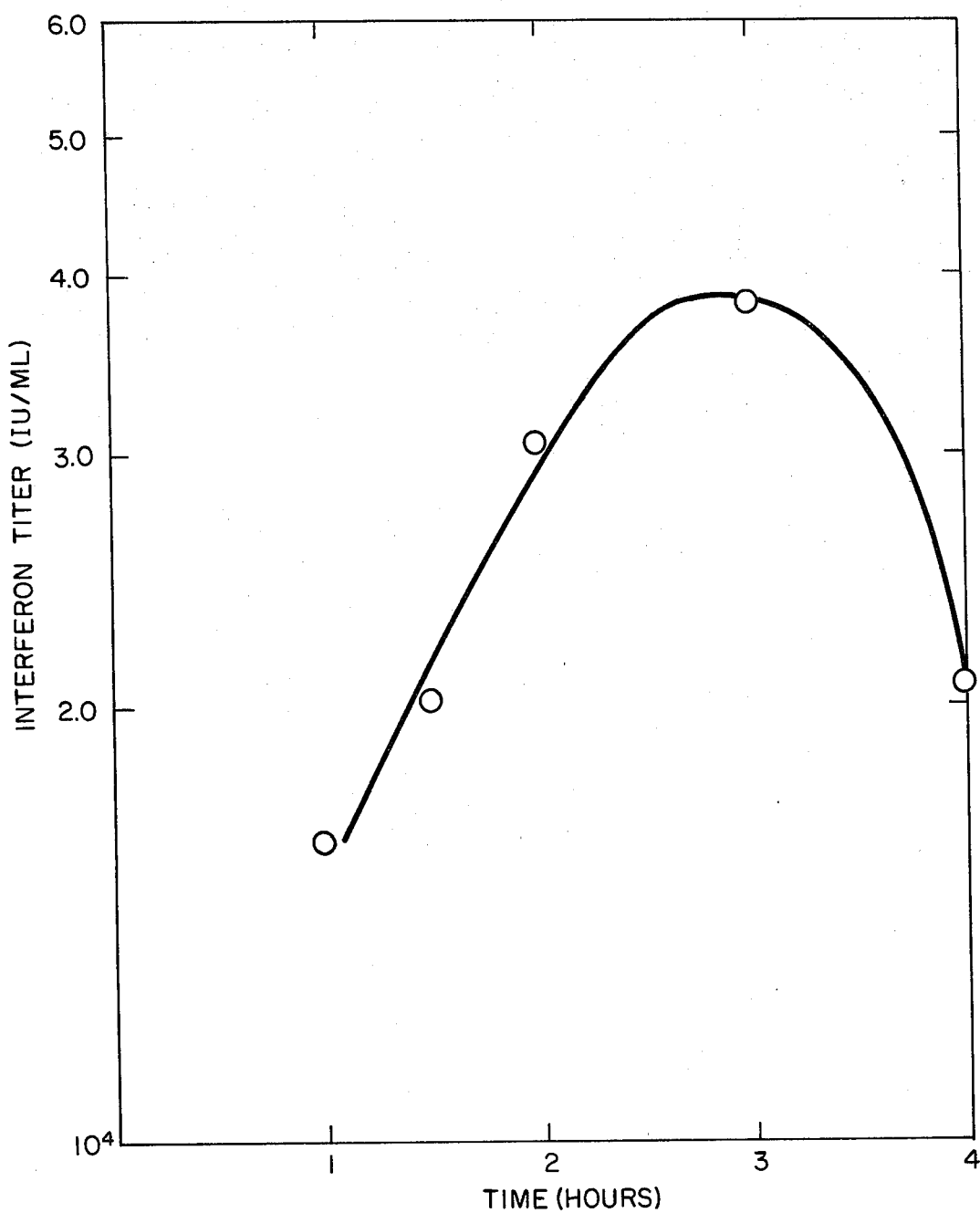
FIG. 2 is a plot graphically illustrating the effect of time of exposure to the antimetabolite actinomycin-D on interferon yield from FS-4 cells under one set of experimental conditions; and, FIGS. 3, 4 and 5 are each plots graphically illustrating comparative kinetic data for interferon production both with and without a temperature shift during the production phase.

The time of exposure to the antimetabolites was also studied. As a result, it was determined that the microcarrier cultures with FS-4 cells had optimum interferon yields if at least a 5 hour exposure to cycloheximide was employed. Studies also indicated that the time of exposure to actinomycin-D was a significant factor in interferon yield. In studies wherein cycloheximide and poly I-poly C were added to cultures simultaneously and actinomycin-D was added four hours later, it was determined that significant interferon yields could be obtained only after ten minutes of exposure to actinomycin-D and that increasing exposure time beyond one hour, e.g., up to two hours, resulted in further gains in yield. FIG. 2 is a plot of actual data obtained in experiments conducted according to Example 1, below, except that the time of exposure to actinomycin-D was varied. The results indicate that the interferon yield appeared to be increased up to an exposure time of about three hours with actinomycin-D.

In addition to cycloheximide and actinomycin-D, other antimetabolites are suitable. Examples include inhibitors of RNA synthesis such as alpha-amanatin and camptothecin as well as inhibitors of protein synthesis such as puromycin, trichodermin, oxytetracycline, and p-fluorophenylanine are also suitable. See Atherton, K. T. and Burke, D. C., "The Effects of Some Different Metabolic Inhibitors on Interferon Superinduction," *J. gen Virol.*, 41, 229-37, 1978.

The crux of this invention, however, is the temperature switch made during the distinct production phase. Production is started at an initial temperature, which is elevated in terms of the interferon production temperature at which production will be sustained. As an example, it was found with the FS-4 microcarrier cultures that an initial temperature of 37° C. for one hour in the production phase followed by sustained interferon production at 30° C. produced outstanding results. As mentioned previously, the initial period at an elevated temperature often produces an increased rate of interferon production at the elevated temperature and, in addition produces an increased rate at the lower production temperature, and usually a prolonged period of production, as well.

In general, the initial temperature and period should be sufficient to produce the increased rate at the later and lower production temperature. Preferably, the initial temperature is at least about 3° C. above the final production temperature.

In terms of time, studies were made involving the use of an elevated temperature for 1, 2, 3 and 4 hours. The results indicated that one hour was sufficient and that ultimate production fell off if this period were extended. Of course, these temperatures and times will vary with the specific cells and other culture parameters involved.

The reason that the ultimate production can be so significantly enhanced by using a temperature shift in the production phase is not understood. One possible explanation for the improvement in yields resulting from the temperature manipulation is that the interferon mRNA is somehow stabilized by lowering the temperature and that the initial period at 37° C. is required in order to provide the high initial production rate which is then sustained or decreases gradually over a long period of time. Two possible ways in which interferon mRNA could be stabilized are: (1) a direct stabilizing effect on interferon RNA of lowering its decay rate, i.e., increasing its half-life; or (2) indirect stabilization by interferring with the ability of a repressor protein to inactivate interferon mRNA.

The latter possibility could involve interference at one or more levels of repressor protein activity, including production of repressor protein mRNA, translation of repressor protein mRNA, or interaction of the repressor protein with interferon mRNA. The fact that increased yields can be achieved even after four hours at the elevated temperature would tend to rule out the first and second possibilities, since four hours would seem to be sufficient time for the repressor protein to be produced. It tends to support the third possibility, i.e., that the repressor protein is less effective in shutting off or inactivating interferon mRNA at the lower temperature.

The invention can be further and more specifically described by the following examples.

EXAMPLE 1

Human diploid foreskin cells (FS-4) were employed. The cells were obtained at approximately the 18th population doubling and were actually used in the experiments between the 30th and 40th population doublings. Stock cultures of these cells were prepared in plastic roller bottles containing Dulbecco's Modified Eagle's Medium (DMEM) supplemented with 10% fetal bovine serum. Antibiotics used were penecillin (100 units/ml) and streptomycin (100 $\mu$g/ml). These stock cultures were maintained in a walk-in incubator at 37° C. until needed.

The roller bottle cultures of FS-4 cells were split 1:2 two days prior to inoculation of microcarriers. Forty-eight hours after the 1:2 split, the cells were dispersed with a solution of trypsin-EDTA (0.1%/0.02%) and seeded onto microcarriers suspended in DMEM plus 5% fetal bovine serum at a concentration of $3\text{-}4\times10^5$ cells ml. Prior to use, the microcarriers were sterilized in glass bottles by autoclaving. Microcarrier concentration was 5 grams/liter, the culture size was 5 liters, and cultures were formed in 14-liter fermenters. The cultures had a pH of about 7.3 and a temperature was maintained at 37° C. After three days of incubation, 50% of the growth medium was removed and replaced with fresh growth medium. After five days, the cells had reached post exponential growth and had a density of about $1\times10^6$ cells/ml.

The post exponential growth cells were primed with interferon. This was done by removing the cells from the growth medium, washing the cells with DMEM, without serum, and then incubating the cells for 16 hours in DMEM containing 0.5% human plasma protein (HPP) and 50 units interferon/ml.

Subsequently, the cells were induced by first withdrawing the priming medium, washing two times with DMEM and then replacing the medium with DMEM containing 50 $\mu$g/ml poly I-poly C plus 10 $\mu$g/ml cyclohexamide. The temperature during the entire induction period was 34° C. After four hours of incubation, actinomycin-D was added to give a final concentration of 1 $\mu$g/ml. After two additional hours of incubation, the medium was removed and the cells were washed two times with DMEM.

Production medium comprising DMEM plus 0.5% HPP was warmed to 37° C. and added to the cells. The culture was incubated at 37° C. for one hour after which the temperature was lowered to 34° C. Culture fluids were collected after 24 and 48 hours of production. Culture fluids were clarified by centrifugation at 2,000 rpm for ten minutes at 5° C. and samples were then removed for assay.

The interferon assay is one described by Havell and Vilcek, ibid. In this procedure, samples were assayed in duplicate in CoStar 96-well culture dishes. Growth medium (100 $\mu$l) was added to each well and two-fold dilutions of each sample were made in duplicate. Each well was seeded with $50\times10^3$ FS-4 cells in 100 $\mu$l growth medium and dishes were incubated for 20-24 hours in a humidified incubator at 37° C. supplied with 10% $CO_2$. Cells were then challenged with 1,000 PFU per well of VSV (Indiana strain). Several wells in each dish served as cell and virus controls. Dishes were incubated at 37° C. and scored microscopically after 48-72 hours. The highest dilution of the samples showing a 50% destruction of cells was considered the end point.

An internal standard calibrated against the International Standard GO23-901-527 was included with each assay.

Cells in microcarrier cultures were enumerated by counting nuclei using a modification of the method of Sanford et al. as described by vanWezel. See Sanford, K. K. et al., "The Measurement of Proliferation in Tissue Cultures of Enumeration of Cell Nuclei," *J. Nat. Cancer Inst.*, 11, 773–95, 1951 and vanWezel, A. L., "Microcarrier Cultures of Animal Cells," in *Tissue Culture: Methods and Applications*, pp. 372–7, Ed. Kruse and Patterson, Academic Press, Inc., New York, 1973. Roller bottle cell counts were made by dispersion with a trypsin-EDTA solution, followed by counting with a hemacytometer.

The results of two runs were:

| Run | Interferon Production (Units/$10^6$ Cells - 24 hours) | |
|---|---|---|
| | First 24 Hours | Second 24 Hours |
| 1 | 24,000 | 24,000 |
| 2 | 65,000 | 45,000 |

Figure 3:
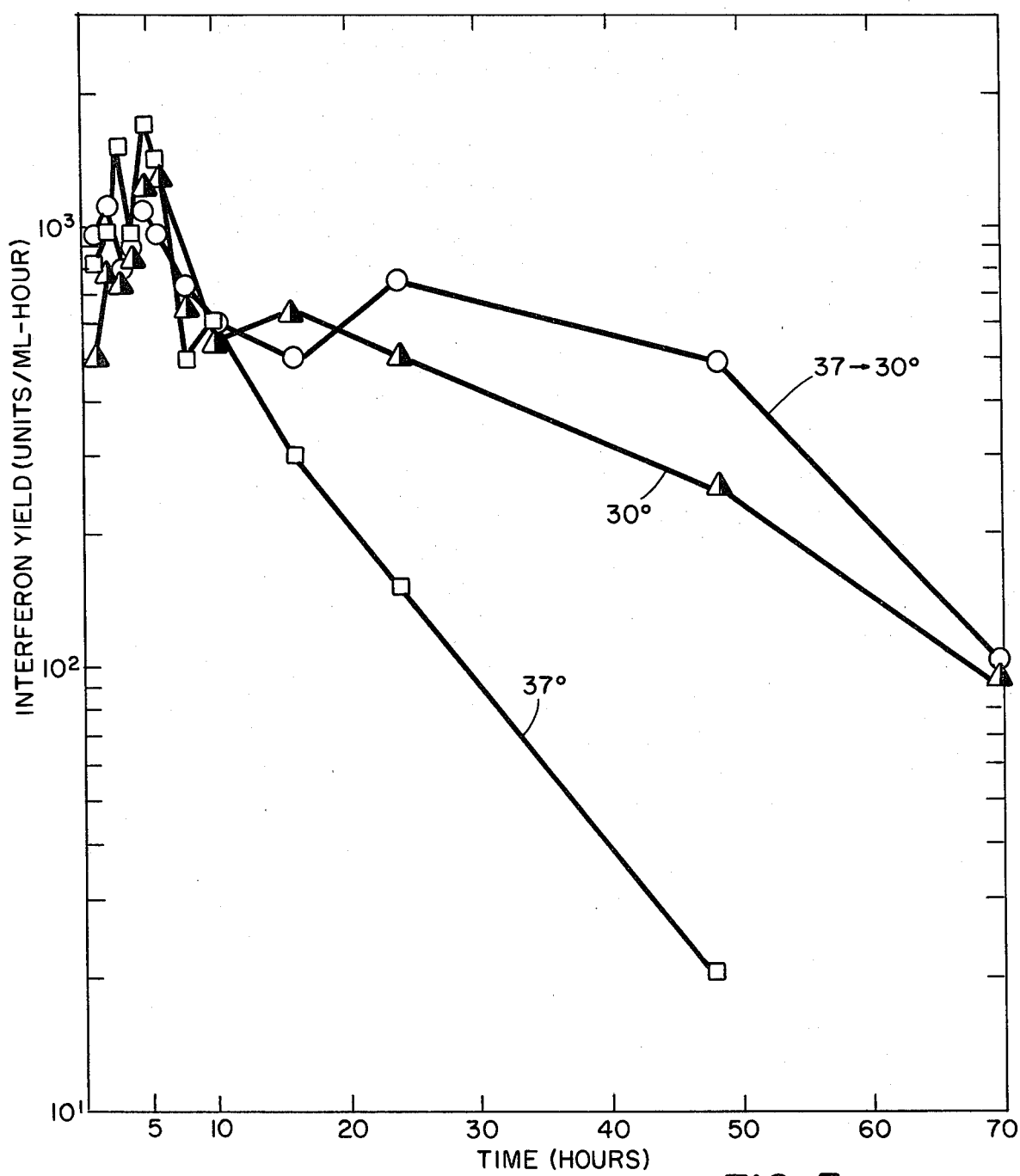
Figure 4:
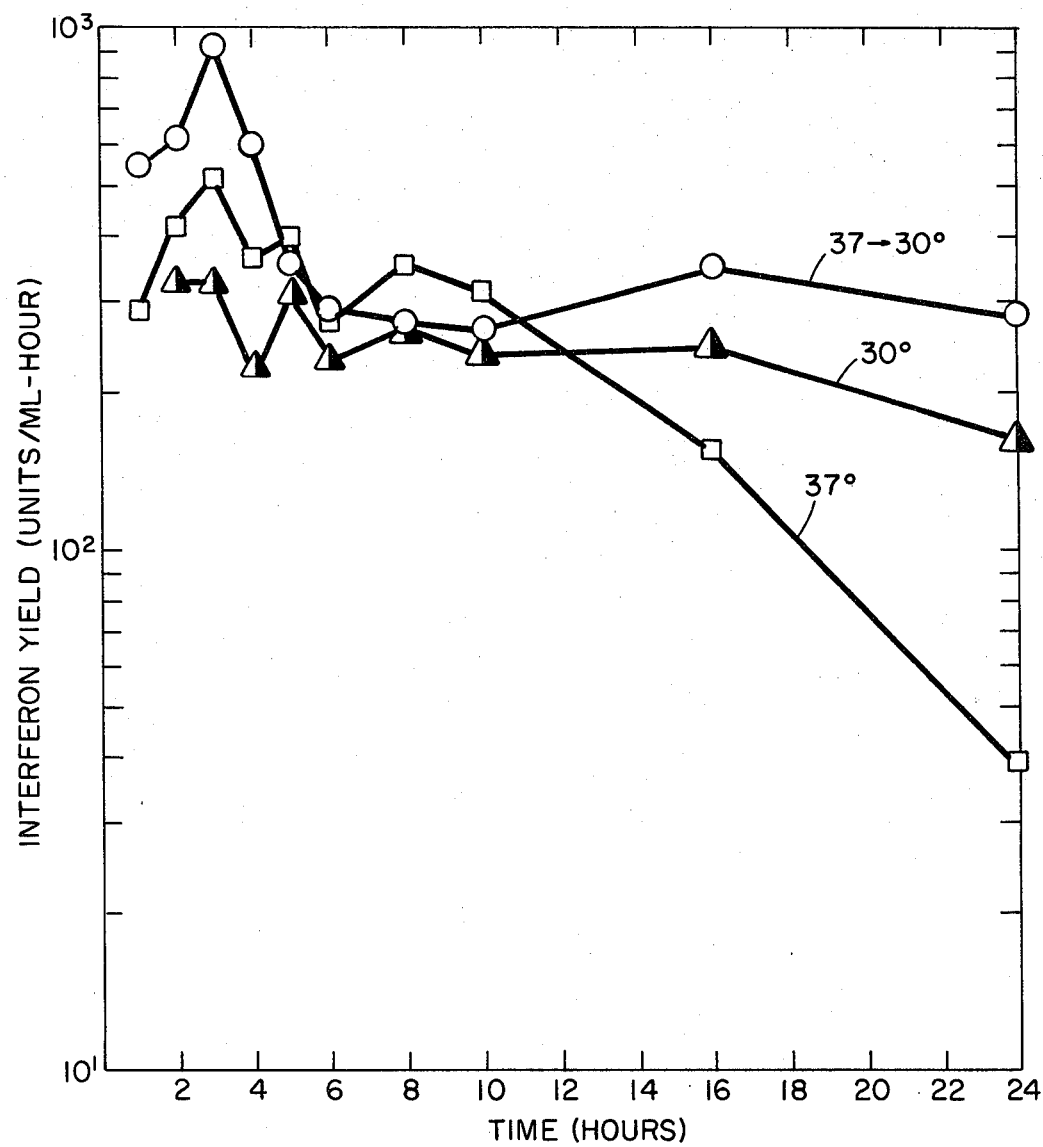
Figure 5:
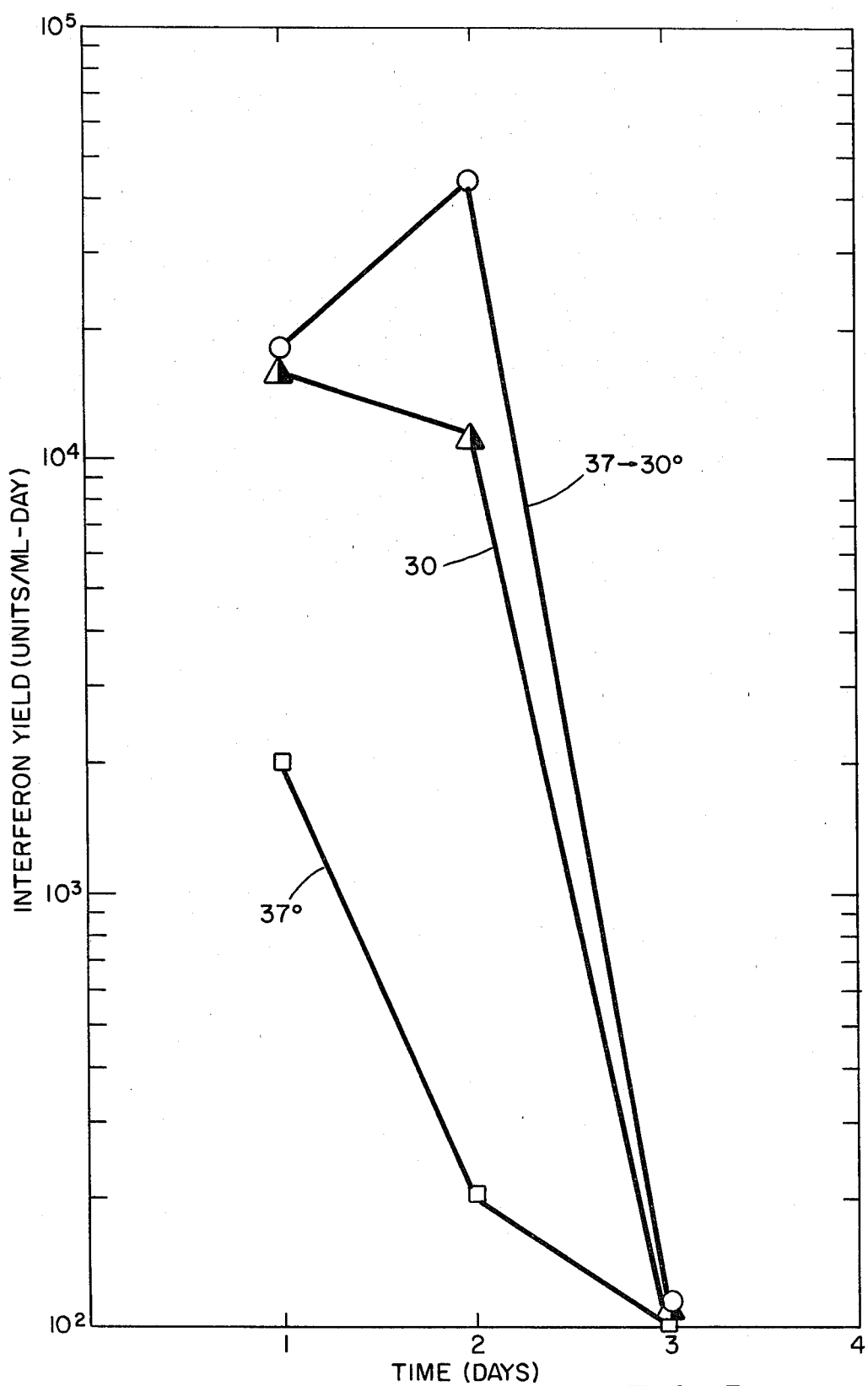

FIG. 3 presents a plot including the data from a run according to this Example as well as comparative runs using the same experimental conditions except that the comparative runs were done with uniform production temperatures of 30° C. and 37° C. FIG. 4 presents similar comparative data for similar experiments wherein the exposure time to actinomycin-D was one hour and the elevated production temperature was maintained for 3 hours. FIG. 5 presents data from similar comparative experiments in which exposure to actinomycin-D was one hour and the elevated temperature during production was maintained for two hours, and the cultures were sampled on a daily basis.

EXAMPLE 2

A series of experiments were conducted to show the effect of various temperature shifts during the production phase. The procedures and materials of Example 1 were employed except for the following differences. The incubation with actinomycin-D was reduced from two hours to one hour. Production was initially started at 37° C., and after two hours the temperature was shifted as indicated for the balance of the production period. The cells were primed with 50 units per ml of interferon for sixteen hours at 37° C. prior to induction.

The results of these temperature studies are as follows:

| Temperature Conditions (°C.) | | Interferon Yield (IU/ml) |
|---|---|---|
| Induction | Production | |
| 34 | 37 | 30,000 |
| 34 | 37 → 34 | 46,000 |
| 34 | 37 → 30 | 54,000 |
| 34 | 37 → 25 | 22,000 |

Since cell density was $1 \times 10^6$ cells/ml, the yield figures also could be stated as units per $10^6$ cells.

EXAMPLE 3

Studies were made to determine the effect of the time of temperature shift during production phase employing the conditions and materials of Example 2. The results were:

| Temperature Conditions (°C.) | | Interferon Yield (IU/ml) |
|---|---|---|
| Induction | Production | |
| 34 | 37 | 15,800 |
| 34 | 37 → 30(1 hr) | 43,400 |
| 34 | 37 → 30(2 hr) | 37,500 |
| 34 | 37 → 30(3 hr) | 28,100 |
| 34 | 37 → 30(4 hr) | 36,300 |
| 34 | 30 | 12,300 |

INDUSTRIAL APPLICABILITY

The invention described herein is useful in the production of interferon, especially interferon from normal human diploid fibroblast cells. Interferon, in turn, is useful as an antiviral agent, immunoregulatory agent, agent for effecting cell division, and anticancer drug.

EQUIVALENTS

Those skilled in the art will recognize, or be able to ascertain using no more than routine experimentation, many equivalents to the specific embodiments of the invention described herein. Additionally, it should be noted that it is believed that the temperature switch described herein could also be useful in the production of other induced cell products, such as enzymes and hormones. Such equivalents are intended to be encompassed by the following claims.

We claim:

1. In the production of interferon induced in cultured animal cells involving distinct induction and production phases, the improvement of initiating the production, at an elevated temperature, maintaining the elevated temperature for at least about one hour and subsequently reducing the temperature by at least about 3° C. to provide a reduced temperature for the balance of the production, said reduced temperature being maintained for a period of time sufficient to produce a majority of the interferon.

2. In the production of interferon including induction of cultured animal cells to stimulate interferon production followed by maintenance of said induced cells at an interferon-production temperature selected to sustain interferon-production, and wherein an antimetabolite is added to the cell culture during said induction and subsequently removed to thereby establish a distinct interferon-production phase:

The improvement wherein the temperature during said distinct interferon-production phase is initially elevated at least about 3° C. above the selected interferon-production temperature for a period of at least about one hour to provide an increase sustained interferon-production rate after the elevated temperature is reduced to said selected interferon-production temperature, said selected interferon-production temperature being maintained for a period of time sufficient to produce the majority of the interferon.

3. The improvement of claim 1 wherein said cells comprise fibroblast cells.

4. The improvement of claims 1 or 3 wherein said cells are cultured on microcarriers suspended in cell culture medium.

5. The improvement of claim 4 wherein said elevated temperature is maintained for less than 4 hours after initiation of said distinct interferon production phase.

6. A method of producing interferon, comprising:

(a) forming a cell culture of interferon-producing animal cells;
(b) introducing an interferon-inducer into said cell culture in an amount sufficient to induce interferon production by said cells thereby initiating an induction period;
(c) introducing an antimetabolite into said cell culture to effectively block the interferon production during said induction period;
(d) removing said antimetabolite from said cell culture to initiate a distinct interferon production phase at a first temperature; and,
(e) after interferon production at said first temperature for at least about one hour, reducing the temperature of said cell culture by at least 3° C. to a second temperature sufficient to sustain interferon production, said second temperature being maintained for a period of time sufficient to produce the majority of interferon.

7. A method of claim 6 wherein said interferon inducer comprises a non-viral inducer.

8. A method of claim 7 wherein said interferon producing cells comprise fibroblast cells.

9. A method of claim 8 wherein said elevated temperature is maintained for a period of less than 4 hours before reducing the temperature.

10. A method of claim 6, 8 or 9 wherein said cells are cultured on microcarriers suspended in cell culture medium.

11. A method of claim 10 wherein said interferon inducer comprises polyinosinic-polycytidylic acid.

12. A method of claim 11 wherein said antimetabolite includes actinomycin-D.

13. A method of claim 12 wherein the induced cells are exposed to actinomycin-D for a period of at least one hour.

14. A method of claim 13 wherein said interferon production phase is continued for at least 48 hours.

15. A method of producing interferon in a culture of interferon-producing animal cells, comprising:
(a) forming a suspension of cell culture microcarriers in a cell culture medium;
(b) inoculating interferon-producing animal fibroblast cells into said suspension of microcarriers to thereby form a cell culture of interferon-producing animal fibroblast cells;
(c) maintaining said cell culture under conditions whereby said cells grow to a high cell density;
(d) introducing an interferon inducer into said cell culture in an amount sufficient to induce interferon production by said fibroblast animal cells thereby initiating an induction period;
(e) introducing an antimetabolite into said cell culture to effectively block interferon production during said induction period;
(f) removing said antimetabolite from said cell culture to initiate a distinct interferon-production phase at a first temperature; and,
(g) after interferon production at said first temperature for at least about one hour, reducing the temperature of said cell culture by at least about 3° C. to a second temperature sufficient to sustain interferon production for a prolonged period, said second temperature being maintained for a period of time sufficient to produce the majority of interferon.

* * * * *